United States Patent [19]
Betsill et al.

[11] Patent Number: 5,163,818
[45] Date of Patent: Nov. 17, 1992

[54] AUTOMATIC CONSTANT AIR FLOW RATE PUMP UNIT FOR SAMPLING AIR

[75] Inventors: Harry E. Betsill, Cockeysville, Md.; William A. Cook, Wilmington, Del.

[73] Assignee: Ametek, Inc., New York, N.Y.

[21] Appl. No.: 476,131

[22] Filed: Feb. 5, 1990

[51] Int. Cl.⁵ .................... F04B 25/00; F04B 49/00
[52] U.S. Cl. ........................ 417/18; 417/20; 417/22; 73/863.03
[58] Field of Search ............. 417/18, 20, 22; 73/863.03

[56] References Cited

U.S. PATENT DOCUMENTS

| | | | |
|---|---|---|---|
| 4,063,824 | 12/1977 | Baker et al. | 417/43 |
| 4,123,932 | 11/1978 | Baker et al. | 73/28 |
| 4,269,059 | 5/1981 | Baker | 73/28 |
| 4,384,825 | 5/1983 | Thomas et al. | 417/22 |
| 4,389,903 | 6/1983 | Bertone et al. | 73/863.03 |
| 4,432,248 | 2/1984 | Lalin | 73/863.03 |
| 4,527,953 | 7/1985 | Baker et al. | 417/38 |
| 4,532,814 | 8/1985 | Lalin | 73/863.03 |
| 4,576,054 | 3/1986 | Lalin | 73/863.03 |

OTHER PUBLICATIONS

Operating Manual for HFS513 Air Sampling System (Silian) pp. 3–29.
Instrument Corp-Air Sampling Equipment and Supplies-Price Guide and Catalogue pp. 3–18.

Primary Examiner—Richard A. Bertsch
Assistant Examiner—David W. Scheuermann
Attorney, Agent, or Firm—Amster, Rothstein & Ebenstein

[57] ABSTRACT

An air sampling device comprises a pump assembly including a pump and a motor operably associated with the pump, the air flow rate of the assembly being substantially characterized by a function having a plurality of measurable variables; sensors for periodically automatically monitoring the variables; a programmable computer operably associated with the sensors for periodically estimating the instantaneous air flow rate of the pump from the function and the monitored variables and for camparing the calculated instantaneous air flow rate with a previously programmed desired air flow rate; and a DC-DC converter responsive to the computer and operably associated with the motor for modulating the motor speed in response to the computer to thereby cause the instantaneous air flow rate of the pump to approach the desired air flow rate.

15 Claims, 8 Drawing Sheets

AUTOMATIC CONSTANT AIR FLOW RATE PUMP UNIT FOR SAMPLING AIR

FIELD OF THE INVENTION

The present invention is directed to an air sampling pump unit, and in particular to an automatic air sampling pump unit that operates at a pre-selected air flow rate by continuously monitoring and adjusting the actual air flow rate through the pump unit.

BACKGROUND OF THE INVENTION

Air sampling pump units having a controlled constant air flow rate are typically used to monitor air to which workers are exposed. These pump units are well known in the art and typical examples of such pumps are disclosed, for example, by Baker et al. in U.S. Pat. Nos. 4,063,824; 4,123,932; 4,269,059; and 4,527,953; by Thomas et al. U.S. Pat. No. 4,384,825; and by Lalin in U.S. Pat. Nos. 4,432,248; 4,532,814; and 4,576,054.

One type of such prior art sampling pump uses a feedback control system based on a pressure switch connected across a variable orifice to measure the air flow rate and vary the pump rate to maintain a constant flow rate. The operator adjusts the variable orifice to set the desired operating flow rate. A separate flow calibration device is used in a trial and error fashion to achieve the desired flow rate.

Another type of such prior art pump uses pump variables such as motor current and RPM to compensate for variations in flow rate. The operator must use a separate flow calibration device and set the sample pump at a flow rate using the same trial and error method as above and then operate the pump at various pressure drops while setting two more variable resistors to set up the compensation circuit for proper functioning at that flow rate. This circuit, when carefully adjusted for proper flow and proper compensation, then compensates to keep flow errors to less than about plus or minus 5%, but at only one flow rate.

Both of these sample pump units lack a means of accurately indicating the pre-adjusted flow rate. Some use a rotameter to indicate flow rate; however they are difficult to read accurately and can be relied upon to produce only plus or minus 20% accuracy.

In view of the drawbacks associated with these conventional air sampling pump units, there is a need for one that can be easily and quickly set to the desired flow rate, that continuously displays in a direct reading format the set flow rate, and that accurately controls flow at that flow rate without further adjustments of the flow compensation circuit, thus eliminating the need for trial and error set-up, thus saving operator set-up time.

SUMMARY OF THE INVENTION

In accordance with the present invention, an air sampling device is disclosed, comprising a pump assembly including a pump and a motor operably associated with the pump, the air flow rate (output) of the assembly being substantially characterized by a function having a plurality of measurable variables; means for operator input of a desired air flow rate; sensors for continuously automatically monitoring the variables; a programmable computer operably associated with said means for operator input and with sensors for continuously estimating the instantaneous output of the pump from the function and the monitored variables and for comparing the calculated instantaneous output with a desired output; and a DC-DC converter responsive to the computer and operably associated with the motor for modulating the motor speed in response to the computer to thereby cause the instantaneous output of the pump to approach the desired output.

DETAILED DESCRIPTION OF THE INVENTION

Figure 1:
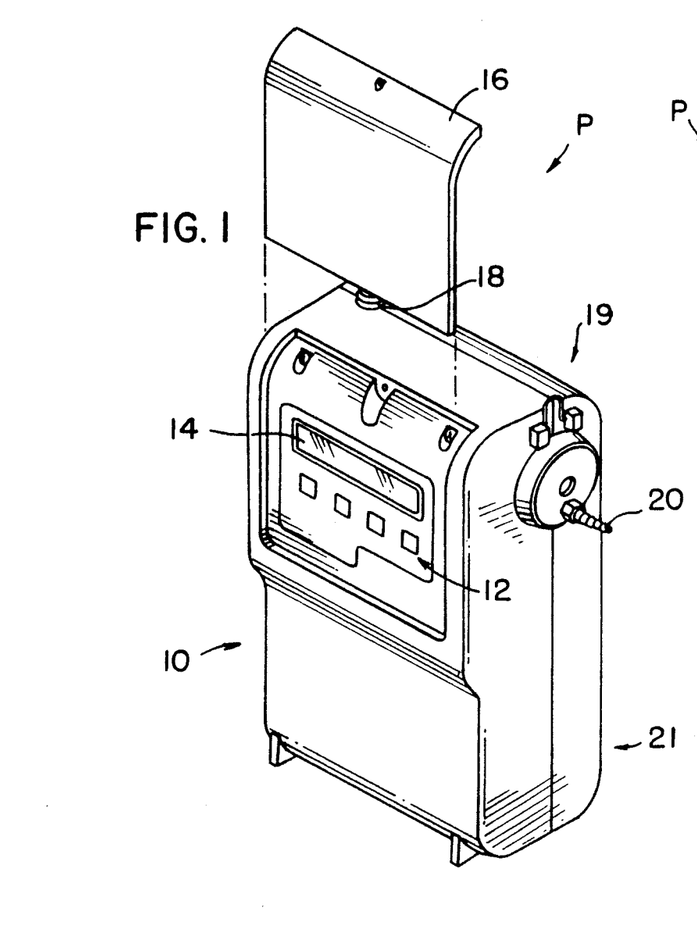
FIG. 1 is a front perspective view of the present invention showing the front cover removed therefrom.
Figure 2:
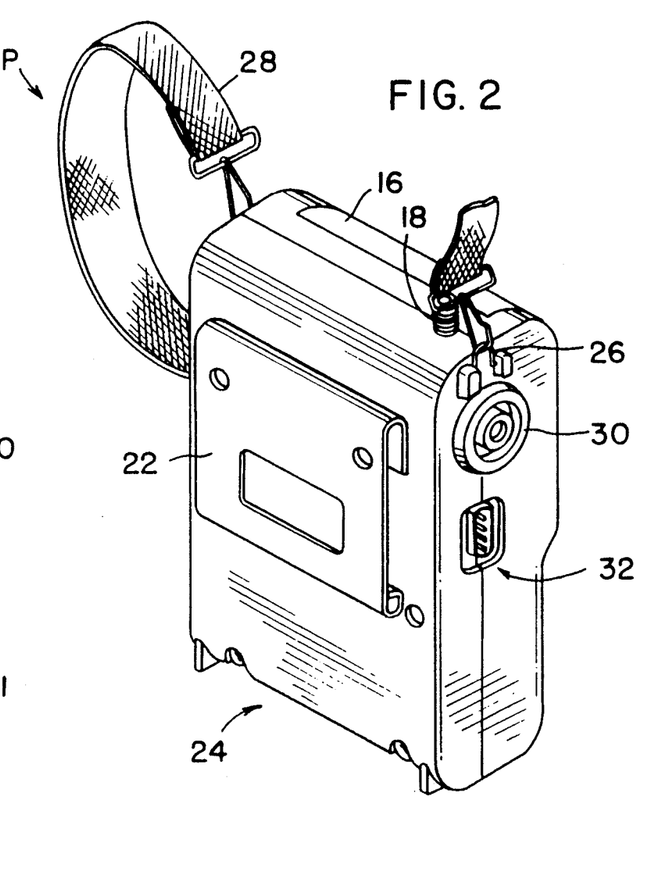
FIG. 2 is rear perspective view of FIG. 1, showing a fragmentary view of a carrying strap attached thereto.
Figure 3:
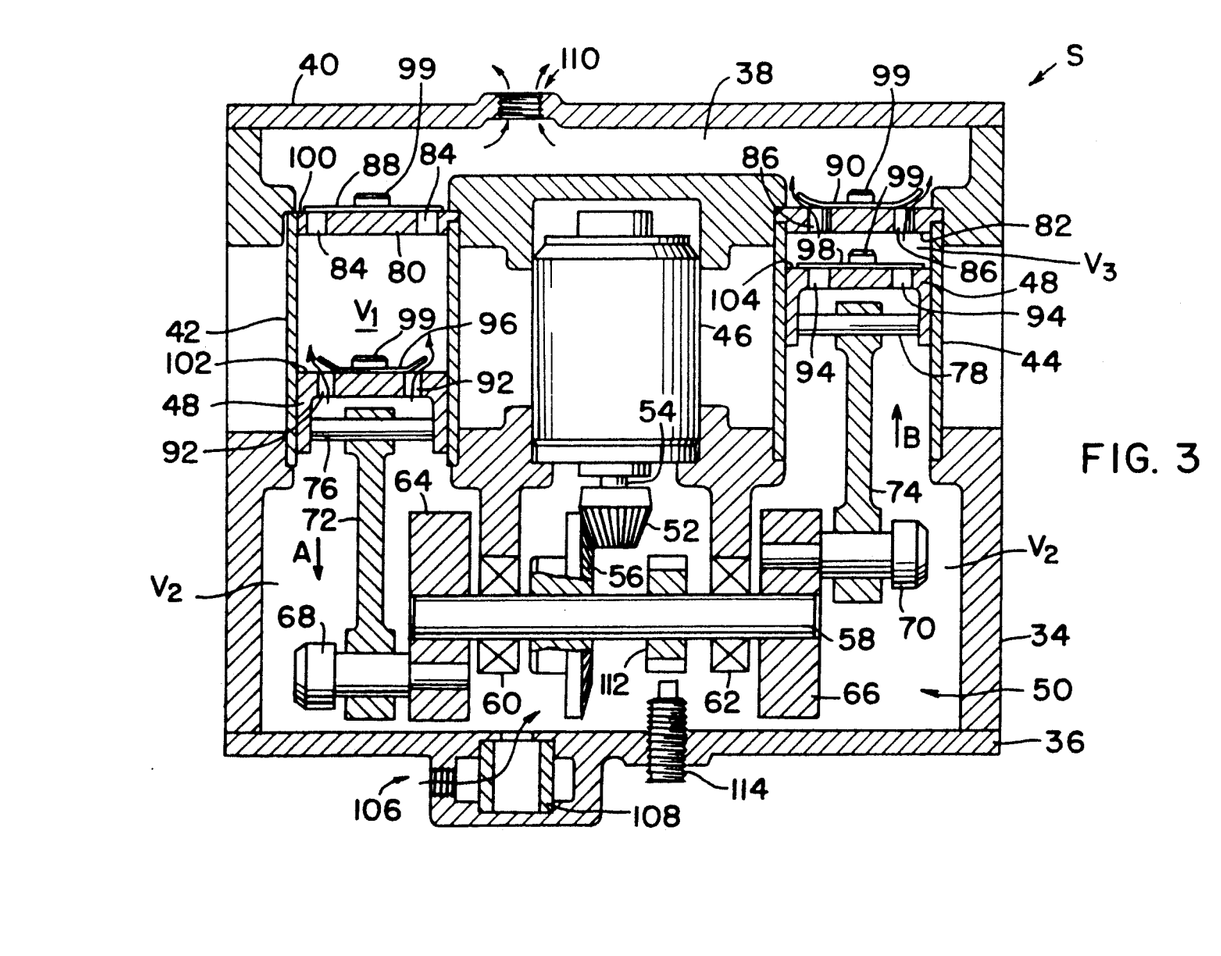
FIG. 3 is a side view of a pump sub-assembly of the present invention, with portions shown in cross-section.

FIGS. 1, 2 AND 3

The present invention provides the ability to specify flow rate from a key board entry and to maintain that flow rate over a range of suction pressures. The approach of the present invention is to utilize a constant displacement pump mechanism, and characterize the pump over the desired flow profile. From the performance data, an equation is derived which relates flow rate to motor current, voltage, and RPM (revolutions per minute) for various suction pressures. The present invention includes a pump mechanism which has the required deterministic qualities.

As illustrated in FIGS. 1 and 2, the air sampling pump unit P of the present invention is of a compact size and is designed for individual use. Preferably, pump unit P measures about $5.94 \times 11.43 \times 17.63$ cm and weighs about 800–1100 grams depending on the weight of the battery pack used in connection with the unit.

The pump unit P can be used to monitor air which may contain environmental hazards to which individuals may be exposed. For example, vinyl chloride vapors can be monitored in a work place, toxic radon gas and related gases in mines can be monitored, and coal dust in mines and pits can also be monitored. The filter used in connection with the pump unit P is then analyzed for the substance being monitored.

Referring back to FIGS. 1 and 2, pump unit P includes on its front face 10 a key pad 12 and an LCD display 14. For protection, a cover 16 may be slid over keypad 12 and LCD display 14. An inlet hose barb 18 is provided on the top 19 of pump unit P. An exhaust hose barb 20 may be provided on the side, the left side as illustrated 21 of pump unit P. In order to facilitate easy carrying the pump unit P on a person, a belt clip 22 is mounted on rear face 24 of the unit. The pump unit P further includes spring clips 26 for attaching a shoulder strap 28 or the like. In FIG. 2, reference numeral 30 designates a cap for a replaceable internal air filter used by pump unit P. The reference numeral 32 designates a connector for optionally attaching data processing accessories to pump unit P. Although not shown, an air sampling bag can easily be attached to pump unit P by a tubing to exhaust hose barb 20. Preferably, the pump unit P is self-contained and includes a battery pack (not shown) for supplying the necessary power for the running of the pump unit.

FIG. 3 illustrates in cross-section various components of the pump sub-assembly S housed within the pump unit P. The pump sub-assembly S includes a crankcase housing 34 with its cover 36, and exhaust manifold 38 with its cover 40. Mounted between crankcase 34 and exhaust manifold 38 are two cylinders 42 and 44 and a D.C. electric motor 46 disposed therebetween. Various elastomeric seals including "O" rings and gaskets (not shown), are provided at various joints and connections in order to insure an airtight pump sub-assembly.

Each cylinder 42 and 44 includes a closely fitted piston 48. The materials used for making piston 48 and cylinders 42 and 44 are preferably rigid and have a low and approximately equal coefficient of thermal expansion. In this manner, negligible air leakage between piston external diameter wall and the cylinder inside diameter wall is achieved over a wide temperature range without the need for piston rings or other types of secondary seals conventionally used. This specific arrangement is advantageous in that sealed, sliding action can be obtained without excessive sliding friction losses. Preferably, each cylinder 42 and 44 is made of a glass, available under the trademark PYREX, and each piston 48 is made of a specially sintered graphite material.

The pistons 48 of each cylinder 42 and 44 are caused to move up and down inside corresponding cylinders by a shaft drive train 50. The drive train action includes motor 46 turning a small bevel pinion gear 52 mounted on motor output shaft 54. The motor 46 is a high efficiency DC motor. Bevel pinion gear 52 engages with a mating bevel gear 56 mounted on crankshaft 58. Bevel gears 52 and 56 preferably have a ratio of about 3:1. The theoretical displacement of the pump unit P is nominally 3.5 cc per revolution; however, the displacement may vary depending upon the pump volume. The crankshaft 58 is mounted in crankcase housing 34 on two anti-friction bearings 60 and 62. Two crankdiscs 64 and 66 are mounted at corresponding ends of crankshaft 58. Crankpins 68 and 70 are mounted on crankdiscs 64 and 66, respectively. As shown in FIG. 3, crankpins 68 and 70 are positioned at 180° relative to each other. Preferably, crankpins 68 and 70 are hard metal shoulder screws which provide a suitable journal bearing surface for corresponding connection rods 72 and 74. The connecting rods 72 and 74 convert the rotating action of crankshaft 58 to a reciprocating motion at corresponding piston 48 in a conventional manner. Preferably, connecting rods 72 and 74 are made of a plastic material with good bearing property so that it may run with little or no lubrication against crankpins 68 and 70 and the hard metal piston pins 76 and 78. A plastic material, such as one sold under the trademark "DELRIN" is a suitable choice. Alternatively, one or both ends of connecting rods 72 and 74 may be designed to incorporate a ball joint that provides additional degrees of freedom, which in turn can provide compensation for any lateral misalignment occurring from manufacturing or assembly tolerances.

Cylinders 42 and 44 include exhaust plates 80 and 82, respectively. Exhaust valve ports 84 and 86 are provided in exhaust plates 80 and 82. Exhaust plate reed valves 88 and 90 are mounted on corresponding exhaust plate 80 and 82, and in their unstressed, flat position substantially close exhaust valve ports 84 and 86. Similarly, pistons 48 are also provided with piston valve ports 92 and 94 covered by corresponding piston reed valves 96 and 98. The reed valves 88, 90, 96 and 98 are mounted by conventional fasteners 99.

OPERATION OF PUMP SUB-ASSEMBLY

As shown in FIG. 3, on the left side, piston 48 is on the downward stroke indicated by arrow A. When the downward stroke of piston 48 first begins near the top dead center adjacent exhaust plate 80, piston 48 momentarily is at a zero velocity and no displacement of air occurs. Under these circumstances, reed valve 88 on the exhaust plate 80 and the piston reed valve 96 on the top surface 102 of piston 48 will both be in their unstressed, flat position.

The action of piston 48 and cylinder 44 (shown on the right hand side of FIG. 3) will be opposite to the action of piston 48 and cylinder 42 combination described above. Since crankpins 68 and 70 are positioned 180° relative to one another, while piston 48 shown on the left hand side of the drawing is descending, piston 48 shown on the right hand side of the drawing is ascending, shown by arrow B.

As illustrated, piston reed valve 96 was opened and the cylinder 42 volume $V_1$ was filled with air from crankcase volume $V_2$, to almost the same pressure that existed inside the crankcase 34. On the other hand, when piston 48 of cylinder 44 is in the ascending mode, the closed volume $V_3$ inside cylinder 44 is decreased and the pressure is increased. This action immediately creates a pressure differential so as to close piston reed valve 98 onto the top surface 104 of piston 48. The pressure, however, continues to increase as the piston 48 moves upwardly. As this action continues, at some point the pressure inside cylinder 44 exceeds the pressure inside the exhaust manifold 38 which typically is at atmospheric pressure. When this occurs, exhaust reed valve 90 is deflected upwardly thereby opening exhaust valve ports 86, and the air from within cylinder 44 flows out therefrom to exhaust manifold 38 via ports 86.

In the manner described above, the air is transferred from crankcase volume $V_2$ to the exhaust manifold 38 at each stroke of the two pistons 48. The air from the exterior is drawn into the pump sub-assembly S through the external sampling device and via a tubing connection into inlet port 106 because of the reduced pressure suction in crankcase volume $V_2$. A replaceable protective filter 108 is built into inlet port 106 to protect the pump components from ingesting any contaminants and harmful debris. After passing through pump sub-assembly S, the air sampling flow is exited through exhaust manifold exit port 110. Although under the normal circumstances, the air flowing out of exhaust port 110 is released to the atmosphere, a sample collecting bag (not shown) may be connected to port 110 via a tubing for further analysis.

In the embodiment disclosed herein, the pump is intended for a portable, battery operation at suction pressures of up to a maximum of about 50 inches water column (W.C.). In this type of arrangement, maintaining low friction and good efficiency is important to obtain adequate operating life with acceptable battery weight. Accordingly, the choice of the low friction piston-cylinder combination is preferable. In addition, it is further preferable to use thin, light weight reed valves made of a plastic sheet, available under trademark MYLAR, over metal materials, to provide efficient valve action with minimum differential pressure. It will be apparent to those of ordinary skill in the art that the upper surfaces of exhaust plate 80 and 82, and upper surfaces 102 and 104 of piston 48, need be substantially flat and well finished to minimize any leakage through corresponding ports 84, 86, 92 and 94.

In the embodiment disclosed herein, inlet and exhaust ports 106 and 110 have been positioned on different surfaces of pump sub-assembly, however, it is well within the scope of the art to provide both inlet and exhaust ports on the same surface.

In FIG. 3, reference numeral 112 designates a tachometer anvil and numeral 114 designates a magnetic tachometer pickup. Preferably, tachometer anvil 112 is a multi-lobed piece of a soft ferromagnetic material and is conveniently made from a piece of twelve tooth steel gear pinion stock. The tachometer anvil 112 in combination with tachometer pickup 114 generates twelve electrical pulses for each revolution of crankshaft 58. An electrical control circuit (described below) uses this data to compute the number of piston strokes per minute and serves to control the motor speed to produce a correct air flow for the specified sampling operation. To allow measurement of a crank RPM a small 12 point spline gear is used as the tachometer anvil for a variable reluctance pickup.

Figure 4:
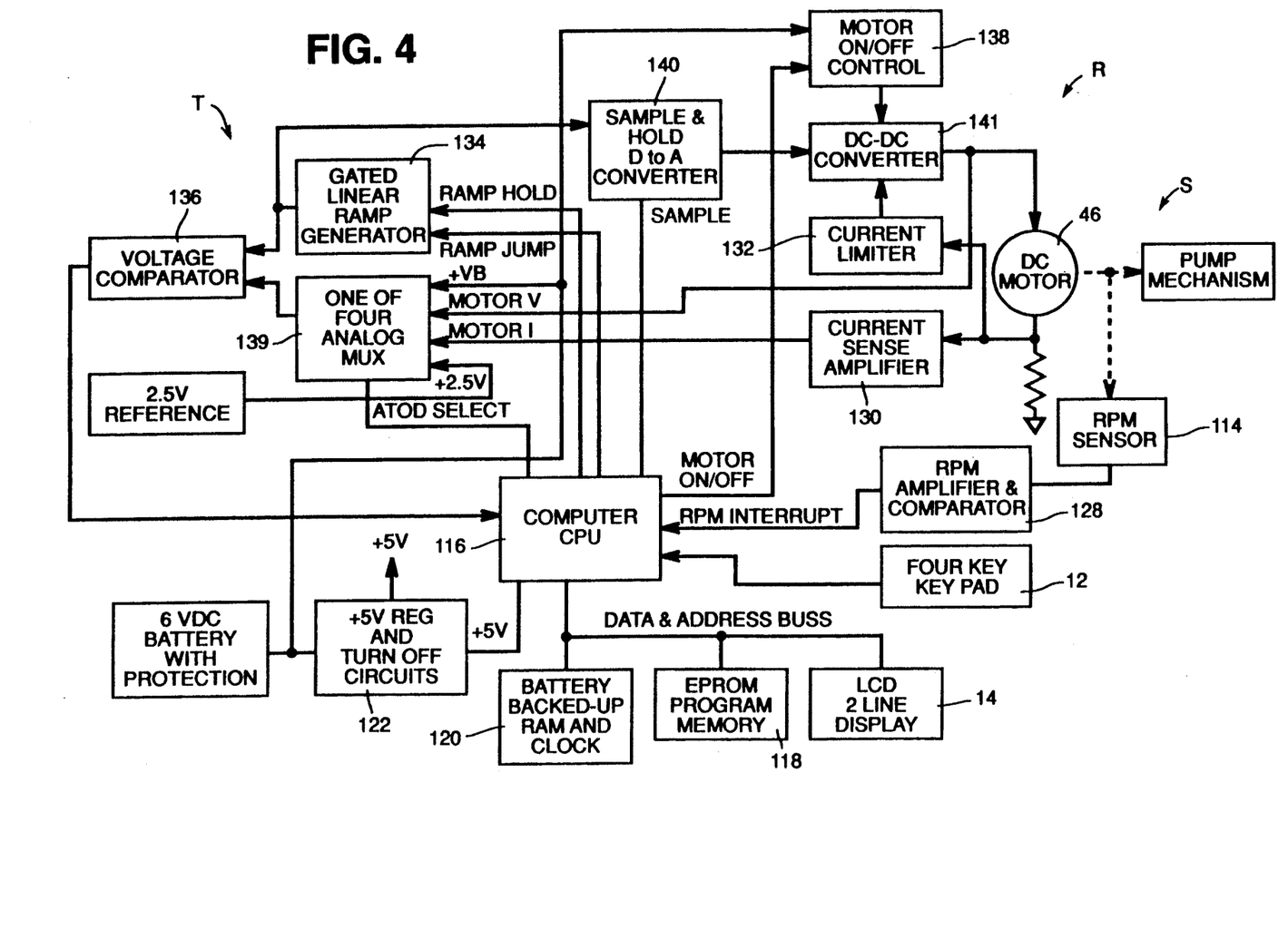
FIG. 4 is a functional block diagram of a control circuit used in the present invention.

FIG. 4

A control circuit R for the operation of the pump unit P is disclosed in FIG. 4.

The pump unit P preferably uses an 80C31 microcomputer 116 with external program memory 118 to provide the user interface and perform flow control. Constants and user programmable variables are stored in a 2k byte battery backed-up RAM 120 with an onboard time of day clock. The user interface is accomplished via the four button keypad 12 and the two line by 16 character dot matrix LCD display 14. All operations are menu driven.

Much of the analog circuitry of the control circuit R is contained in two custom bipolar linear integrated circuits. One of the custom integrated circuits provides diverse functions, including a 5 volt regulator and turn-off circuitry 122, tachometer limiting amplifier and comparator 128, motor current and dc amplifier 130.

The other integrated circuit is primarily associated with the analog to digital converter T and motor control interface. The circuits included are a linear ramp generator 134 with external dump and hold control inputs, ramp comparator 136, motor on/off control 138, and sample and hold gated amplifier circuit block 140 which is used as a digital to analog converter in cooperation with the ramp generator 134.

The analog to digital converter T provides three independent analog to digital conversions and a single digital to analog converter output to the sample and hold circuit block 140. The nominal resolution of both the converters is 12 bits.

The operation of the analog to digital converter T is based on comparison of the voltage across a ramp capacitor in the ramp generator 134 with the voltage to be measured. Time is counted from the start of the ramp until the measured voltage is equal to the ramp voltage. This time interval is thus proportional to the input voltage. The converter T operates in a repeating cycle measuring the time interval of each of four inputs corresponding to a 2.5 volt reference, battery voltage, motor voltage and motor current (converted to voltage) which are fed to a multiplexer 139. Since the converter T is continuously measuring the reference voltage, it can automatically compensate for minor variation in the ramp timing circuitry due to changes in temperature. Each input is allocated 10 milliseconds for a measurement and the ramp generator 134 is adjusted to give a nominal count of 4096 counts for the 2.5 volt reference. This gives a resolution of 12 bits in the measured voltage. The total cycle repeats every 80 milliseconds because an output to the sample and hold gated amplifier circuit block 140 is generated between each analog measurement.

As mentioned above the RPM is sensed by a magnetic pickup 114 coupled to the tachometer anvil 112 located on the crank shaft 58. The voltage from the magnetic pickup 114 is filtered prior to being amplified in semicustom integrated circuits 128. The amplification takes place in a high gain limiter followed by a voltage comparator for interfacing to a hardware interrupt pin on the microcomputer 116.

The motor is preferably driven from a simple DC-DC converter 141 preferably configured around a CA3130 operational amplifier. The input to the DC-DC converter 141 is developed across a sample and hold capacitor (not shown) in circuit block 140 which is driven by the digital to analog converter circuitry in cooperation with the ramp generator 134. The sample and hold capacitor is updated every 20 milliseconds under computer control. The basic operation is to start the linear ramp, and stop it at a predetermined time by raising the ramp hold line. This causes the ramp capacitor to remain at the voltage corresponding to the desired output voltage. The sample and hold amplifier in circuit block 140 is then gated to charge the sample and hold capacitor to a voltage equal to the ramp capacitor.

The DC-to-DC converter 141 incorporates current limit feedback 132 to prevent excessive current drain when the motor 46 is stalled. Since the motor voltage is set in a feedback loop, absolute accuracy of the digital to analog converter 140 is not important.

FLOW CONTROL ALGORITHM

FIGS. 5-12

Figure 5:
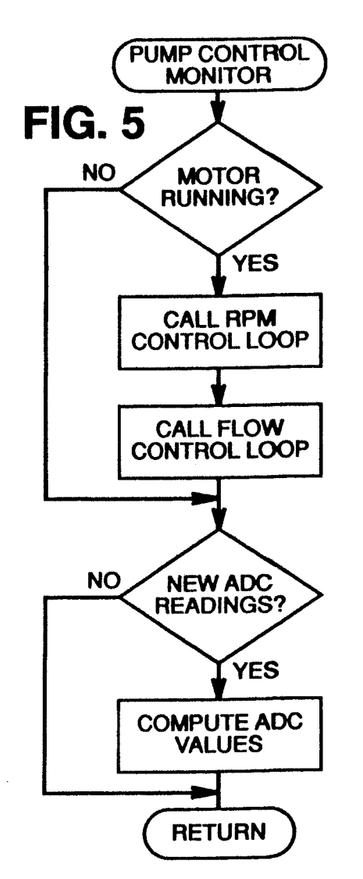
FIGS. 5-12 are flow charts of an algorithm used in the present invention.
Figures 6, 7:
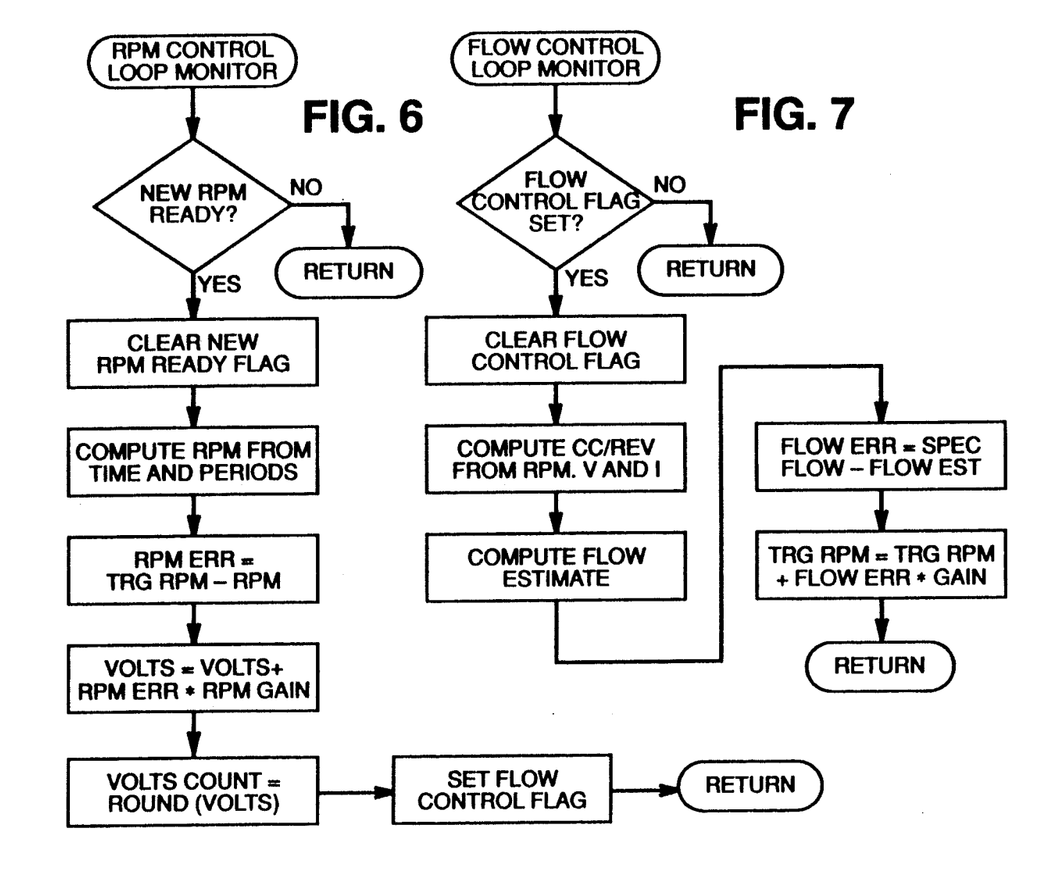

Flow diagrams for the pump unit P are presented in FIGS. 5-12. Flow control is achieved in a negative feedback double loop system, as best shown in FIGS. 5, 6 and 7. The interior loop controls crankshaft RPM by varying the motor voltage while the outer loop controls the desired flow rate by varying the target RPM to the interior loop. The interior loop holds the pump crankshaft 58 at a constant RPM and the outer control loop continuously updates the target RPM. Both loops operate in an integrating mode whereby the control variable is corrected on each pass by summing the error multiplied by a gain constant with the control variable. In a steady state situation no error will exist in either loop.

The primary parameters of the algorithm are motor voltage, motor current and shaft RPM. As described in the above, motor voltage and current are measured using a modified integrating analog to digital converter T with a resolution of approximately 12 bits. Shaft RPM is measured using a magnetic pickup 114 coupled to a tachometer anvil 112 mounted on the crank shaft 58. Motor voltage is controlled by operating the analog to digital converter (ADC) T as a sample and hold digital to analog converter (DAC) 140. Both the RPM and ADC/DAC measurements are made using timer and hardware interrupts available in the microcomputer 116. When readings are available, flags are set to notify the main line code that actions are necessary.

The ADC/DAC circuitry is under direct control of the microcomputer 116 and uses the timing and interrupt capability to measure four inputs and output one voltage. One of the inputs is a 2.5 volt reference used to provide temperature stability. The basic principle is to measure the time from the beginning of a linear ramp until the ramp voltage is equal to the measured voltage. This is done for the three unknown voltages, as well as, the reference voltage. The measured voltage is given by:

$$Vmeas = (Tmeas/Tref)*Vref.$$

where Vmeas is the desired voltage, Tmeas is the time from start of ramp to the point where Vmeas is equal to the ramp voltage, Tref is the time from start of ramp to point where Vref is equal to the ramp voltage, and Vref is the 2.5 volt reference.

Figures 8, 9:
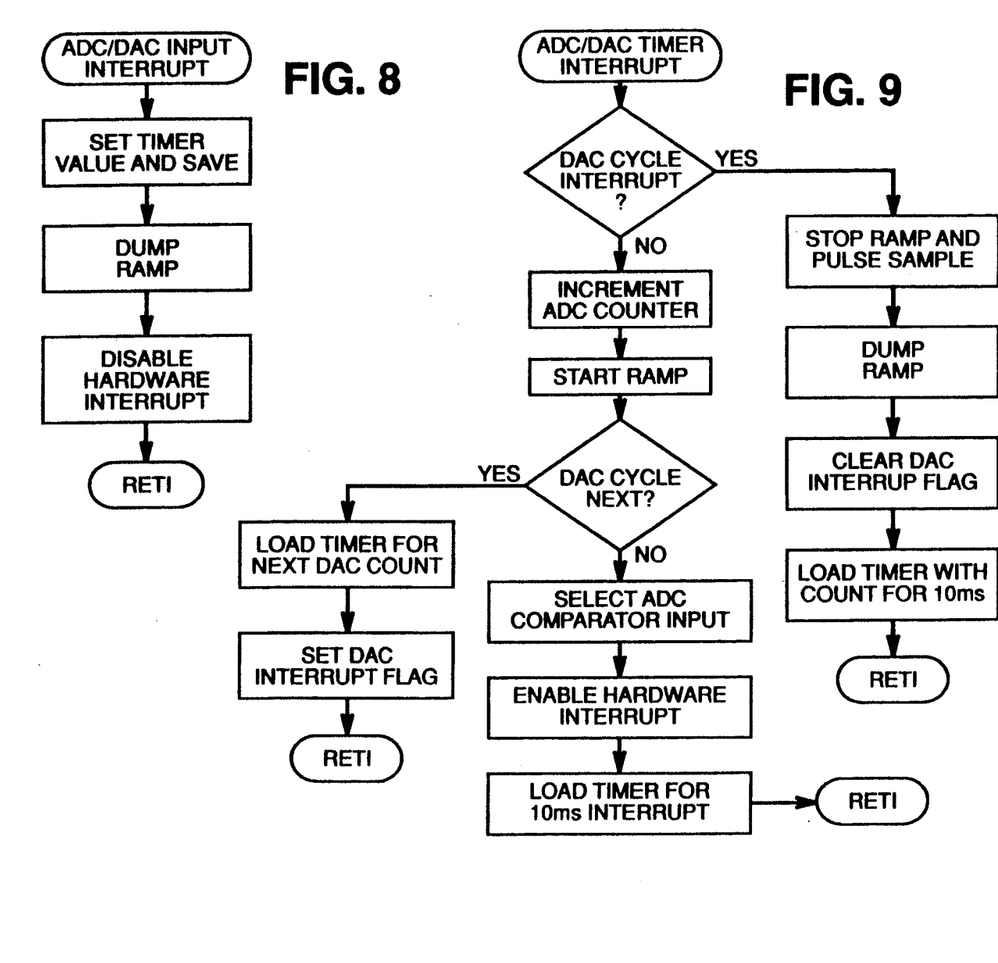
Figure 10:
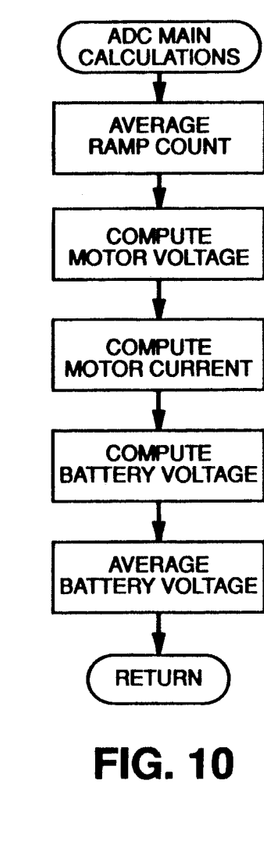

FIGS. 8, 9 and 10 disclose flow diagrams for the timer and hardware interrupt routines. The hardware interrupt is driven by comparator 136 which compares the ramp voltage to the voltage to be measured. The timer routines control the ramp dump and hold outputs from the microcomputer 116. The time for one measurement is set to 10 ms to provide a time base to other functions. The actual active time of one measurement is approximately 8 ms. A complete measurement cycle is made every 80 ms. This cycle is made up of the four measurements alternating with a DAC output. The measured input to the comparator 136 is selected by the computer 116 via a preferably analog CMOS multiplexer 139.

Referring to FIGS. 8, 9 and 10, a measurement is started by the timer interrupt routine. If an ADC cycle is next, the ramp is started, the appropriate input is steered to the comparator 136, and hardware interrupt is enabled. When the ramp voltage is equal to the measured voltage a hardware interrupt occurs, and the timer value is read and stored for later use. The cycle is completed when the timeout value for a 10 ms time base occurs.

A DAC output follows the completion of every ADC measurement. This is started in the timer by loading the timer with the desired output count, starting the ramp and setting the flags appropriately for a DAC output cycle. When the timer interrupt occurs, the ramp is stopped and a sample pulse is generated to transfer the ramp voltage to a sample and hold capacitor in circuit block 140. The voltage across this capacitor is used as a reference input to the DC-DC converter 141 which drives the pump motor 46. The timer is then loaded with the count necessary to complete a 10 ms time base.

On the next timer interrupt the next input voltage in the cycle is selected and ADC measurement is made.

Figure 11:
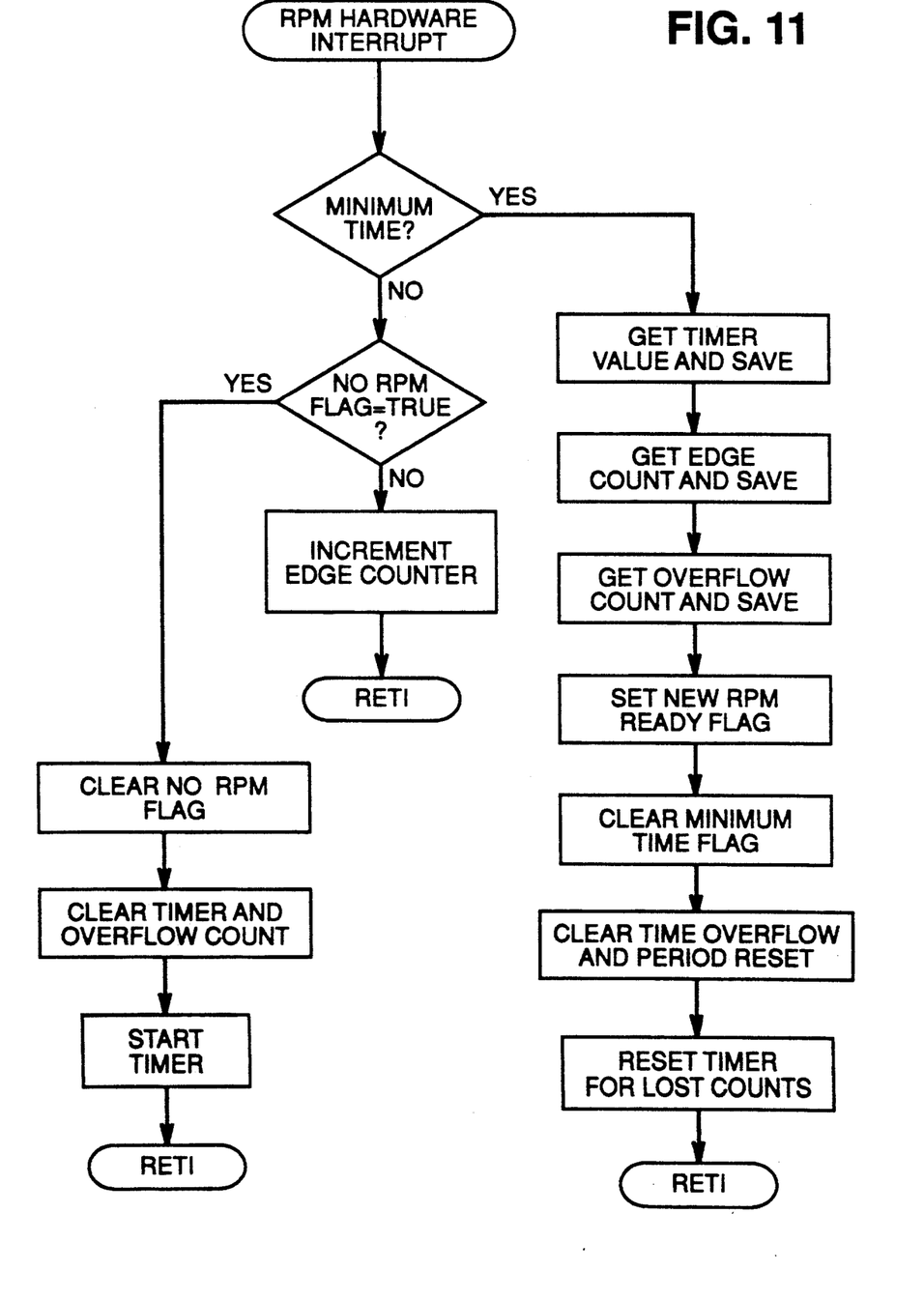
Figure 12:
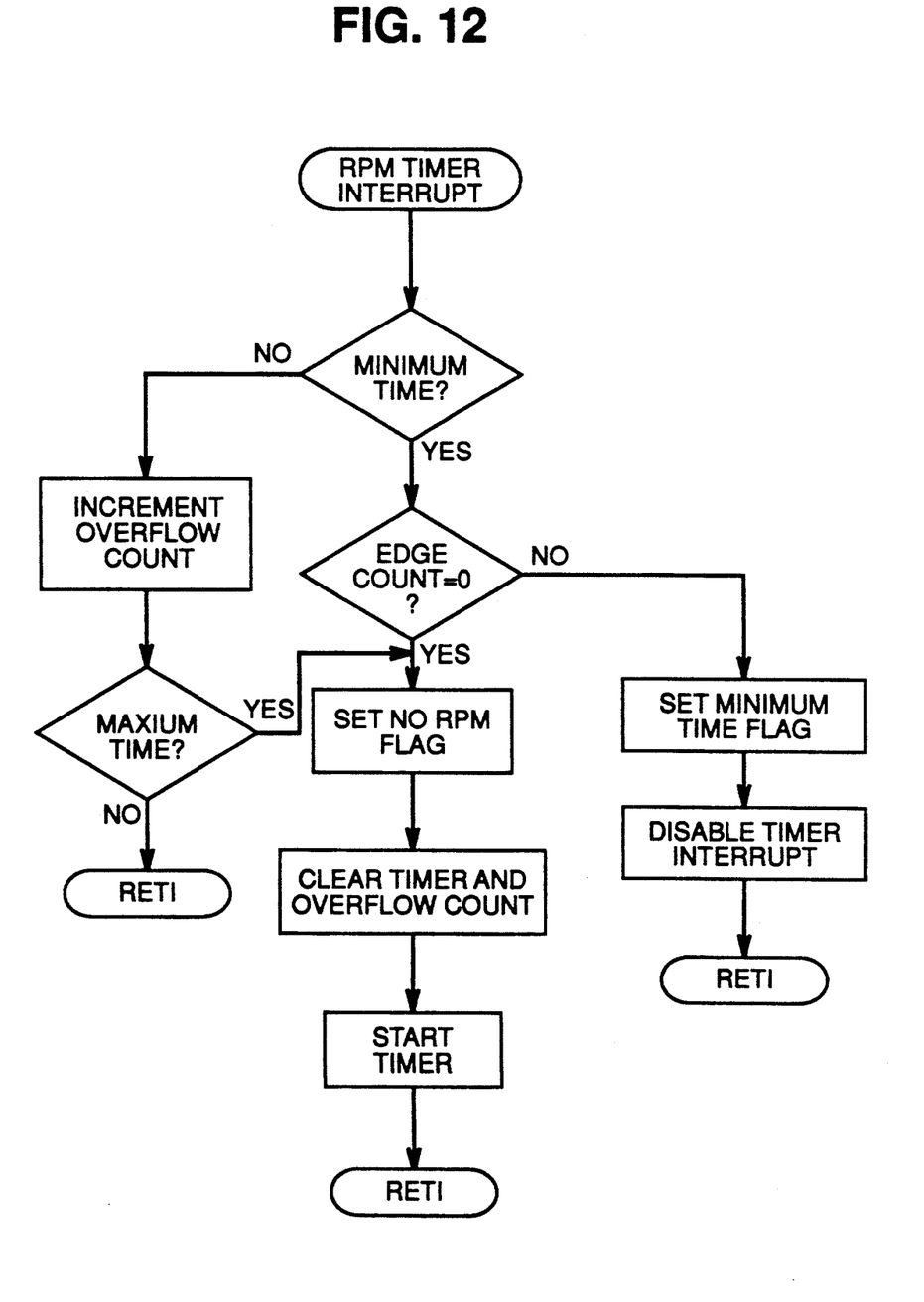

FIGS. 11 and 12 disclose the algorithm for measuring RPM. RPM is measured by synchronizing with falling edge of the tachometer amplifier in circuit block 128 and counting time for an integral number of period. The RPM update rate is typically a minimum of 0.3 seconds, and determines the nominal update rate to both RPM and flow control loops. The algorithm is based on the measurement of time for an integral number of periods of the input frequency. To maintain high resolution in the RPM calculation, a minimum time of approximately 0.3 seconds for each RPM measurement is used. The hardware interrupt routine counts periods, and gets the period count and total time on the first falling edge following the minimum timeout. The time routines determine when the minimum time has occurred and monitors for motor stall. If no period counts occur between the minimum and maximum timeout then a No RPM Flag is set. When the interrupt routine detects the first edge following the minimum timeout, the new RPM flag is set and the parameters of period count, timer value and overflow count are saved for use by the main line routines. Prior to returning, the timer and counter registers are cleared for the next measurement. The main line routines associated with motor control calculate the RPM from period counts and total time.

Flow control is achieved in software as shown in the flow diagrams of FIGS. 5, 6 and 7. When the motor 46 is running the RPM and flow control procedures are called once each monitor pass. The RPM control loop is an interior loop within the flow control loop and responds quickly to variation in RPM. The flow control loop operates more slowly and effects changes in the flow by varying the target RPM to the RPM control loop routine.

The interrupt routines discussed above are continuously running and provide the data necessary for both RPM and flow control. Both loops operate in an integrating mode where the error is sensed, multiplied by a gain constant and added to the control variable. As an example, the control equation for the RPM control loop is, $$Volt\_count = Volt\_count + RPM\_gain*(Target\_RPM - RPM).$$

Volt_count is the control variable which sets the voltage to the motor 46 and is output by the DAC interrupt routines in background mode. RPM_gain is a constant which is negative quantity as necessary for a negative feedback loop. The equation states that the motor voltage is corrected at each update interval by an incremental value which tends to force the RPM to be the target RPM. It is obvious from the equation that Volt_count, in a steady state condition will be forced to a value which will produce no error independent of the Target_RPM. The inner loop thus has the capability of holding a desired RPM. This desired RPM is based on the desired flow rate and the characteristic response of the pump, as discussed below, to flow and suction pressure.

Flow control is handled in a similar fashion based on motor voltage, motor current, shaft RPM and the desired flow. In the outer loop, the characteristic equation, a function of motor current, voltage and RPM, is used to predict the instantaneous flow per revolution (cc per rev). Preferably, a sixth order polynomial is used to estimate the flow per revolution of the crank shaft as CC/REV. The constants for the polynomial are determined for each pump by running load profiles at various RPMs and head pressures. At each point, the motor voltage, motor current, flow rate, along with RPM and pressure are recorded. The data from the characterization is then regressed to calculate the six values for polynomial which best fit the pump unit P. The polynomial constants are stored in the battery backed-up ram 120. The equation used is preferably:

$$CC/REV = A + B*R/V + C*V*I/R + D*R/I + E*I*I/R + F*R,$$

where R is RPM, V is motor voltage, and I is motor current. Once an estimate of CC/REV is available, an estimate of the flow rate is determined by:

$$Flow\_Rate = RPM*(CC/REV)$$

In the flow control loop, the control variable is target RPM which is the reference to the RPM loop. The integrating equation is:

$$Target\_RPM = Target\_RPM + Flow$$
$$gain*(Desired\_flow - Flowrate).$$

Again, the loop will converge to the best estimate of the desired flow which satisfies the polynomial. Under steady state conditions the flow loop will force the pump to a regime which most closely satisfies the characteristic of the pump. The equation is used to determine the target RPM which most closely achieves the desired flow.

It is important to note that because of the integrating loop, only the trends of the polynomial are used for flow control. The loop does not force the pump to exactly follow the characterization, but allows ministration of the error even though variations occur in motor voltage, current and RPM relative to the characterization. The pump is not forced to conform to the characteristic equation, but is allowed to determine the state which most closely fits the equation at that instant. When the loop is under steady state conditions it is operating at what it thinks is the desired flow with no error. Rate limits are imposed on the flow control loop which allow the pump to quickly, but smoothly follow load changes.

The key to the performance of the pump unit P is the repeatability of the pump sub-assembly S. By characterization of the pump sub-assembly S, an equation which estimates pump flow and pressure load as a function of motor voltage, current and RPM can be derived. Good correlation is achieved for a complex equation which relates cc per revolution to motor current, voltage, and RPM. A simpler relationship, with slightly greater error, exists which relates flow to RPM, and suction pressure.

Any time the crankshaft 58 is stopped for greater than 1.0 second, or the average predicted suction pressure exceeds the specified load profile, restricted flow condition is advantageously declared.

Figure 13:
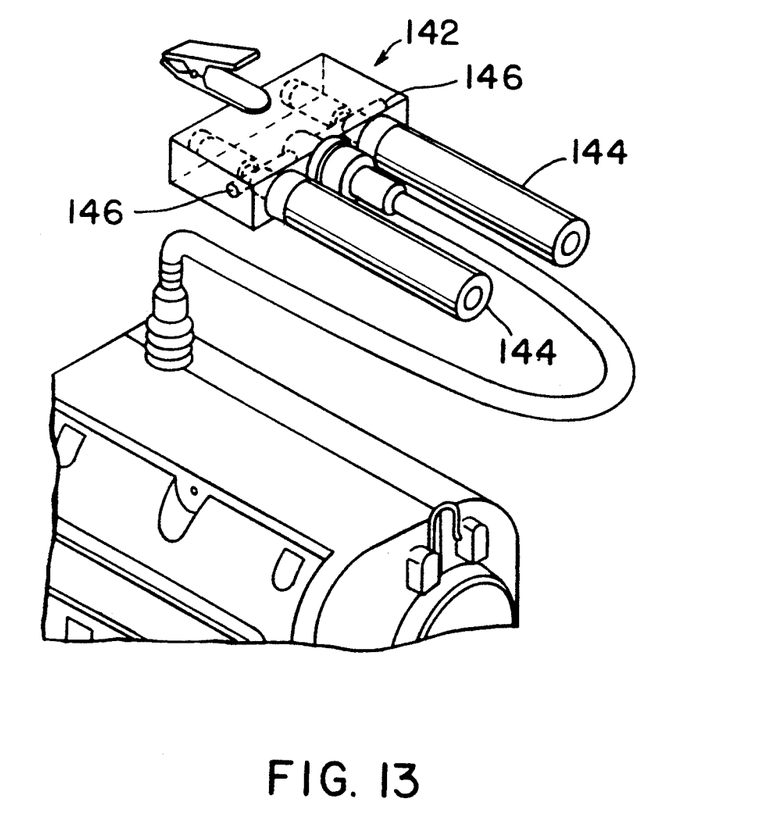
FIG. 13 is a fragmentary perspective view of the present invention showing a low flow sampling manifold.

FIG. 13

The pump unit P is capable of delivering flow rates from 500 cc/minute to 8000 cc/minute with crank rates of 130 to 2200 RPM. Typically, this range is covered with 2 pumps in the slightly different strokes. For low flow sampling under 500 cc/minute, the pump unit P is forced to operate in a constant pressure mode. An embodiment of the present invention for use under 500 cc/minute is disclosed in FIG. 13. A flow bypass is needed in this mode to ensure that the total flow rate is preferably above 1500 cc/minute. A constant pressure intake manifold 142 of standard design with sampling tubes 144 are hooked to the inlet hose barb 18. Up to four sampling tubes 144 may be hooked up. Flow by-passes 146 are disposed on the manifold 142 to divert flow from the sampling tubes 144. Each sampling tube flow path is independently adjustable for flows up to 200 cc/minute. To assist in flow adjustment in each tube, total flow or differential flow is displayed in the LCD display 14.

In this mode the outer loop is modified to calculate instantaneous pressure based on two characteristic equations. The target RPM is then modified based on the error in pressure. The nominal manifold target pressure is 20 inches of water. The calculation first uses motor current, voltage, and RPM to determine the flow rate, as described in the above, and then calculates the pressure from the equation relating flow to pressure and RPM. For example, the following equation relates flow to pressure and RPM.

$$CC/MIN. = RPM*[(V*N) - (W.C.*P)] - [W.C.*L].$$

where RPM is crank RPM, W.C. is suction pressure, V is swept displacement, N is valve efficiency, P is pressure effect, and L is leakage effect. The valve efficiency lumps such effects as headspace losses and the pressure drops and time lags in opening the valves. Pressure effect acts to reduce the delivery of air as the pressure drop across the piston increases. The leakage rate is pressure dependent and represents a time dependent volume loss independent of RPM. The leakage rate could be leakage between the piston on the cylinder or the valve or housing leakage. The constants N, P, and L are derived from graphical plots or by averaging the measured data.

The correction mode is the same as described above whereby the target RPM is updated based on the pressure error. The motor voltage is then controlled to keep the suction pressure constant.

Unit turn-on is achieved by pressing the MENU key on the keypad 12. This depression activates the 5 volt regulator 122 and starts the computer 116. Turn-off is controlled by the computer 116 by selecting the appropriate menu item. The computer 116 issues an output to turn-off the 5 volt regulator 122.

Under standard atmospheric conditions the initial accuracy of the pump unit P is five percent of the desired flow. Slightly greater error can be expected when the pump unit P is operated in non-standard condition. After calibration the error is reduced to less than two percent.

Calibration is achieved by measuring the flow rate with an external standard and entering the measured flow rate in the CAL mode. The computer 116 calculates the correction factor necessary to bring the flow to the desired flow. Since this correction factor is held in the battery backed-up RAM 120, routine calibration should only require that the flow rate be checked for each test.

While this invention has been described as having preferred design, it is understood that it is capable of further modification, uses and/or adaptations of the invention following in general the principle of the invention and including such departures from the present disclosure as come within known or customary practice in the art to which the invention pertains, and as may be applied to the essential features set forth, and fall within the scope of the invention or the limits of the appended claims.

We claim:

1. An air sampling device, comprising:
   a) an air pump assembly including a pump and a motor operably associated with said pump, the air flow rate of said assembly being substantially characterized by a polynomial function having measurable variables of input voltage, current draw and motor speed;
   b) means for operator input of a desired air flow rate;

c) means for periodically automatically monitoring the input voltage, current draw and motor speed;

d) programmable computer means operably associated with the means for operator input and with said monitoring means for periodically estimating the instantaneous air flow rate of said pump from the function and the monitored variables and for comparing the calculated instantaneous output with a desired air flow rate; and e) means operably associated with said computer means for automatically regulating the input voltage to said motor in response to said computer means for modulating the speed of said motor, thereby causing the instantaneous air flow rate of said pump to approach the desired air flow rate.

2. A device as in claim 1, wherein said computer means includes input/air flow rate means for providing interface between the device and a user.

3. A device as in claim 1, wherein:
a) said pump assembly includes a pair of cylinder/piston pumps;
b) each of said cylinders is made of glass material; and
c) each of said pistons is made of graphite material.

4. A device as in claim 1, wherein:
a) said monitoring means includes means for comparing each of the monitored variables with a reference, thereby permitting measurement of the monitored variables;
b) said comparing means includes a voltage comparator and a ramp generator operably associated with said computer means;
c) the input of said comparator includes one of the monitored variables and the air flow rate of said ramp generator; and
d) the air flow rate of said comparator is operably associated with said computer means.

5. A device as in claim 1, wherein said computer means includes a key pad and a display for providing interface between the device and a user.

6. A device as in claim 1, wherein:
a) said motor is a DC motor; and
b) said regulating means includes a DC-DC converter operably associated with said DC motor and said computer means.

7. A device as in claim 1, wherein:
a) said pump assembly includes a crankshaft operably associated with said motor; and
b) said monitoring means includes a speed sensor operably associated with said crankshaft for measuring the motor speed.

8. A device as in claim 7, wherein said speed sensor means includes a tachometer anvil operably associated with said crankshaft and a magnetic pickup device coupled to said tachometer anvil.

9. An air sampling device comprising:
a) an air pump assembly including a pump having at least a cylinder including glass material and a piston including graphite material and a motor operably associated with said pump, the air flow rate of said assembly being substantially characterized by a function having a plurality of measurable variables;
b) means for operator input of a desired air flow rate;
c) means for continuously automatically monitoring the variables;
d) programmable computer means operably associated with the means for operator input and with monitoring means for continuously estimating the instantaneous air flow rate of said pump from the function and the monitored variables and for comparing the calculated instantaneous air flow rate with the desired flow rate;
e) means operably associated with said computer means for automatically regulating one of the variables in response to said computer means for modulating the motor speed to thereby cause the instantaneous air flow rate of said pump to approach the desired air flow rate.

10. A device as in claim 2, wherein said monitoring means includes a speed sensor operably associated with said motor.

11. A device as in claim 9, wherein said monitoring means includes means for comparing each of the monitored variables with a reference, thereby permitting measurement of the monitored variables.

12. A method for operating at a predetermined desired flow rate a pump assembly including a motor, the method comprising the steps of:
a) characterizing the instantaneous flow rate of the pump assembly as a polynomial function of measurable variables by selecting the input voltage, current draw and motor speed as the variables; running the pump under various suction pressures and motor speeds; recording the input voltage, current draw, motor speed and flow data rate; and performing a regression analysis to obtain a best fit equation for relating flow rate as a function of the selected variables;
b) measuring the variables;
c) calculating the estimated instantaneous flow rate from the characteristic polynomial function;
d) comparing the calculated instantaneous flow rate with the desired flow rate;
e) adjusting one of the variables to decrease any variance between the calculated instantaneous flow rate and the desired flow rate; and
f) repeating periodically the steps of calculating, comparing and adjusting.

13. A method as in claim 12, wherein said adjusting includes the step of selecting the input voltage as the adjusted variable.

14. An air sampling device, comprising:
a) an air pump assembly including a pump and a motor operably associated with said pump, the air flow rate of said assembly being substantially characterized by a function having a plurality of measurable variables;
b) means for operator input of a desired air flow rate;
c) means for continuously automatically monitoring the variables including means for comparing each of the monitored variables with a reference, thereby permitting measurement of the monitored variables;
d) programmable computer means operably associated with the means for operator input and with monitoring means for continuously estimating the instantaneous air flow rate of said pump from the function and the monitored variables and for comparing the calculated instantaneous air flow rate with the desired flow rate;
e) means operably associated with said computer means for automatically regulating one of the variables in response to said computer means for modulating the motor speed to thereby cause the instantaneous air flow rate of said pump to approach the desired air flow rate; and wherein said comparing means includes a voltage comparator and a ramp generator operably associated with said computer means, the input of said comparator including one of said monitored variables and the output of said ramp generator and the output of said comparator being operably associated with said computer means.

15. An air sampling device, comprising:

a) an air pump assembly including a pump and a motor operably associated with said pump, the air flow rate of said assembly being substantially characterized by a sixth order polynomial function having measurable variables of input voltage, current draw and motor speed and the suction pressure of said assembly being substantially characterized by an equation dependent on the air flow rate of said pump assembly and motor speed;

b) means for operator input of a desired air flow rate;

c) a constant pressure intake manifold assembly operably associated with said pump assembly;

d) means for periodically automatically monitoring the input voltage, current draw and motor speed;

e) programmable computer means operably associated with the means for operator input and with said monitoring means for periodically estimating the instantaneous suction pressure of said pump from the air flow rate function, the suction pressure equation and the monitored variables and for comparing the calculated instantaneous suction pressure with a desired suction pressure; and f) means operably associated with said computer means for automatically regulating the input voltage to said motor in response to said computer means for modulating the speed of said motor, thereby causing the instantaneous suction pressure of said pump to approach the desired suction pressure.

* * * * *